(12) United States Patent
Ozaki et al.

(10) Patent No.: US 8,154,589 B2
(45) Date of Patent: Apr. 10, 2012

(54) MEDICAL OPERATION SYSTEM FOR VERIFYING AND ANALYZING A MEDICAL OPERATION

(75) Inventors: Takashi Ozaki, Hachioji (JP); Akinobu Uchikubo, Iruma (JP); Koichi Tashiro, Sagamihara (JP); Chie Imamiya, Tachikawa (JP); Takeaki Nakamura, Hino (JP); Masakazu Gotanda, Kanagawa (JP)

(73) Assignee: Olympus Corporation, Tokyo (JP)

( * ) Notice: Subject to any disclaimer, the term of this patent is extended or adjusted under 35 U.S.C. 154(b) by 1343 days.

(21) Appl. No.: 11/351,807

(22) Filed: Feb. 10, 2006

(65) Prior Publication Data

US 2006/0242096 A1 Oct. 26, 2006

(30) Foreign Application Priority Data

Feb. 10, 2005 (JP) ................... 2005-035165

(51) Int. Cl.
*A62B 1/04* (2006.01)
(52) U.S. Cl. .......................... 348/65; 600/118
(58) Field of Classification Search .................. 128/898; 600/103, 522, 501, 118; 348/65, 74
See application file for complete search history.

(56) References Cited

U.S. PATENT DOCUMENTS

| | | | |
|---|---|---|---|
| 2002/0118958 A1* | 8/2002 | Ishikawa et al. | 386/117 |
| 2003/0055356 A1* | 3/2003 | Nonaka | 600/544 |
| 2004/0030367 A1* | 2/2004 | Yamaki et al. | 607/60 |
| 2004/0133390 A1* | 7/2004 | Osorio et al. | 702/178 |

FOREIGN PATENT DOCUMENTS

| | | |
|---|---|---|
| JP | 03-267722 | 11/1991 |
| JP | 2002-233535 | 8/2002 |
| JP | 2002-319092 | 10/2002 |
| JP | 2004-280455 | 10/2004 |

OTHER PUBLICATIONS

Machine English Translation JP 2004-280455 A, Sawazaki et al., Oct. 7, 2004.*
Japanese Official Action dated May 18, 2010.

* cited by examiner

*Primary Examiner* — Nelson D. Hernández Hernández
(74) *Attorney, Agent, or Firm* — Scully, Scott, Murphy & Presser, P.C.

(57) ABSTRACT

A medical operation system includes a controller for controlling a plurality of medical equipments, a communication unit for transmitting and receiving data between each of the plurality of medical equipments and the controller in two-way communications, an information recorder which records, together with time information, information regarding the plurality of medical equipments transmitted and received by the communication unit, a signal processor which extracts predetermined information from the information recorded on the information recorder and processes the predetermined information to generate time-series data, and a display output unit for visualizing the time-series data output from the signal processor and outputting the visualized time-series data to a display.

12 Claims, 7 Drawing Sheets

MEDICAL OPERATION SYSTEM FOR VERIFYING AND ANALYZING A MEDICAL OPERATION

This application claims benefit of Japanese Application No. 2005-35165 filed in Japan on Feb. 10, 2005, the contents of which are incorporated by this reference.

BACKGROUND OF THE INVENTION

1. Field of the Invention

The present invention relates to medical operation systems and, in particular, to a medical operation system verifying and analyzing the content of a medical operation based on a variety of pieces of information recorded on medical operation devices constituting medical equipment.

2. Description of the Related Art

Surgical operations are widely performed using endoscopes.

The endoscope typically is used with an insufflation device for insufflating the abdominal cavity of a patient and a high-frequency cauterization device as a hand instrument for manually cutting and/or coagulating a lesion of the patient. Therefore, during an endoscopic surgical operation, a variety of treatments are performed observing the endoscope.

Among medical operation systems including a plurality of medical operation devices, Japanese Unexamined Patent Application Publication No. 2002-233535 proposes an endoscopic surgical system that includes an endoscope and surgical devices different from the endoscope.

In the known endoscopic surgical system including medical operation devices having the same communication interfaces and the same communication protocol, a system controller generally controls medical operation devices through such communication means.

The known endoscopic surgical system includes an information storage unit storing predetermined data such as system operation history, error history, and comments exchanged between the communication units, and the system controller controls the recording of the predetermined data to the information storage unit.

SUMMARY OF THE INVENTION

Accordingly, it is an object of the present invention to provide a medical operation system verifying and analyzing the content of a medical operation based on information recorded on each medical operation device.

In accordance with a first aspect of the present invention, a medical operation system includes a controller for controlling a plurality of medical equipments, a communication unit for transmitting and receiving data between each of the plurality of medical equipments and the controller in two-way communications, an information recorder which records, together with time information, information regarding the plurality of medical equipments transmitted and received by the communication unit, a signal processor which extracts predetermined information from the information recorded on the information recorder and processes the predetermined information to generate time-series data, and a display output unit for visualizing the time-series data output from the signal processor and outputting the visualized time-series data to a display.

In accordance with a second aspect of the present invention, a medical operation system includes a control function for controlling a plurality of medical equipments in response to a control instruction, a communication function for transmitting and receiving data between each of a plurality of medical equipments and the control function, an information recording function for recording, on a storage unit together with time information, information transmitted from and received by each of the plurality of medical equipments, a signal processing function for extracting required predetermined information from the information recorded on the storage unit and processing the predetermined information to generate time-series data which changes on time axis, and a display output function for visualizing the time-series data and outputting the visualized time-series data to a display.

DETAILED DESCRIPTION OF THE PREFERRED EMBODIMENTS

The embodiments of the present invention are described below.

First Embodiment

Figure 1:
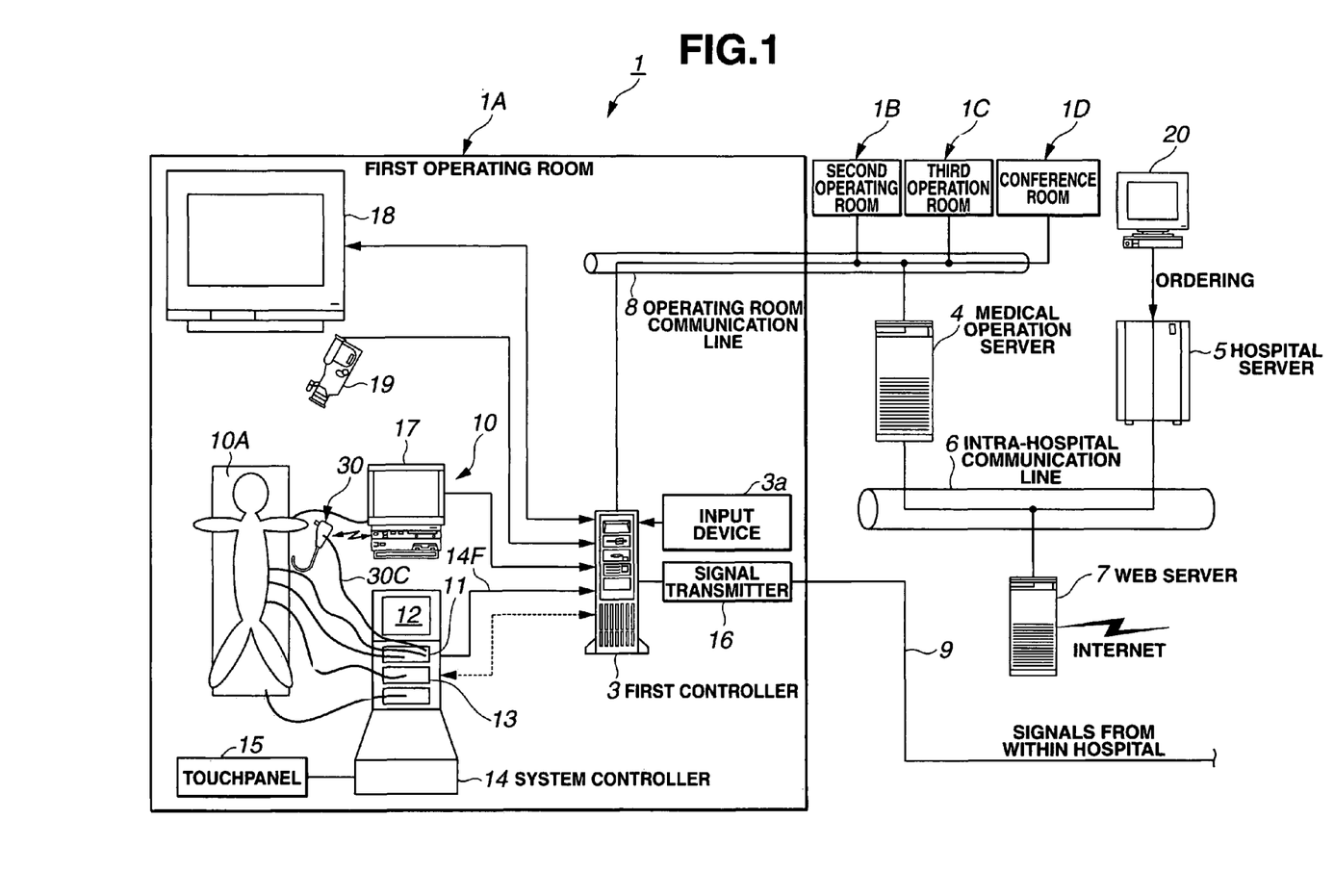
FIG. 1 is a block diagram illustrating an entire configuration of a medical operation system in accordance with a first embodiment of the present invention.
Figure 2:
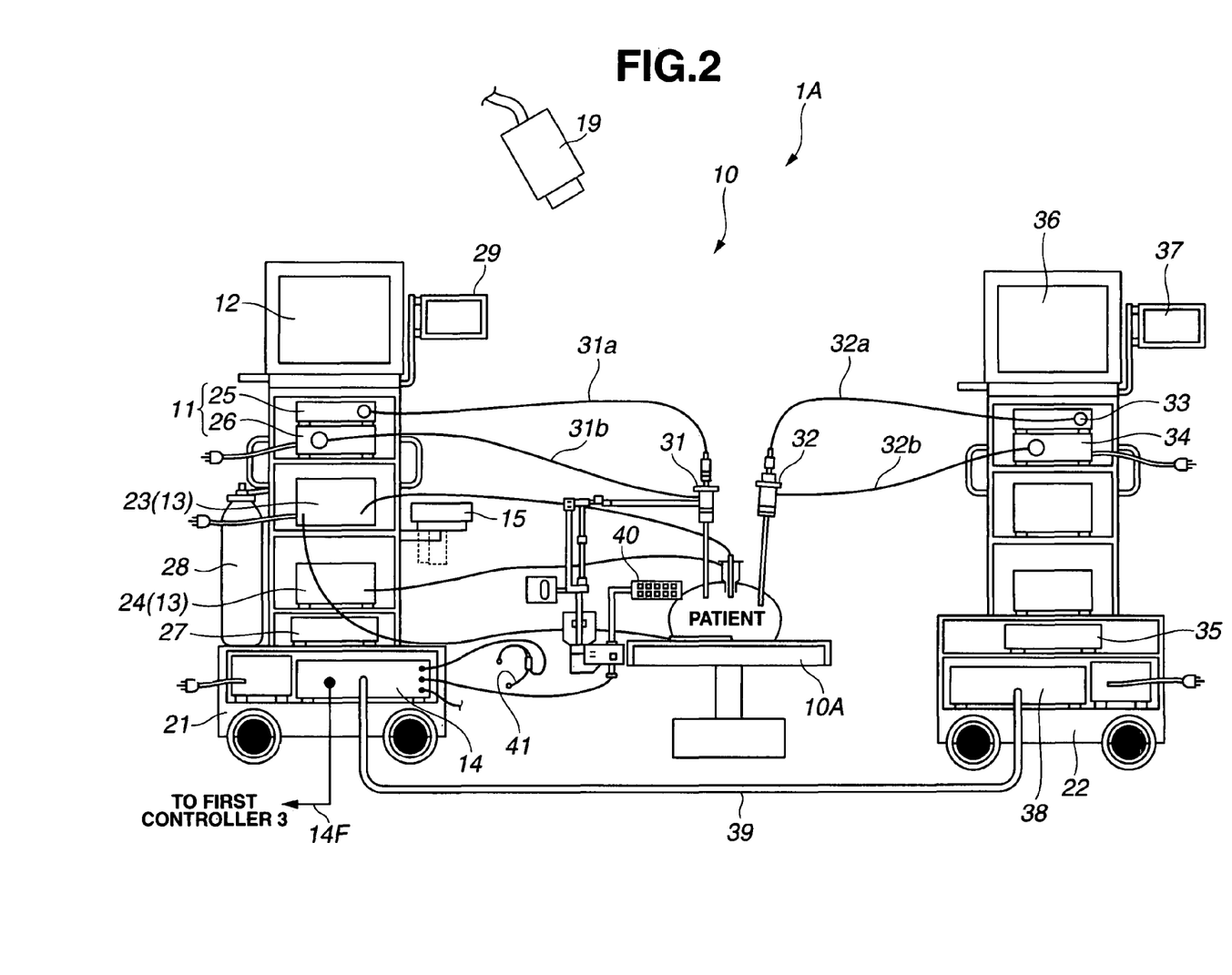
FIG. 2 illustrates a configuration of a specific example of the medical operation system installed in a first operating room of FIG. 1.
Figure 3:
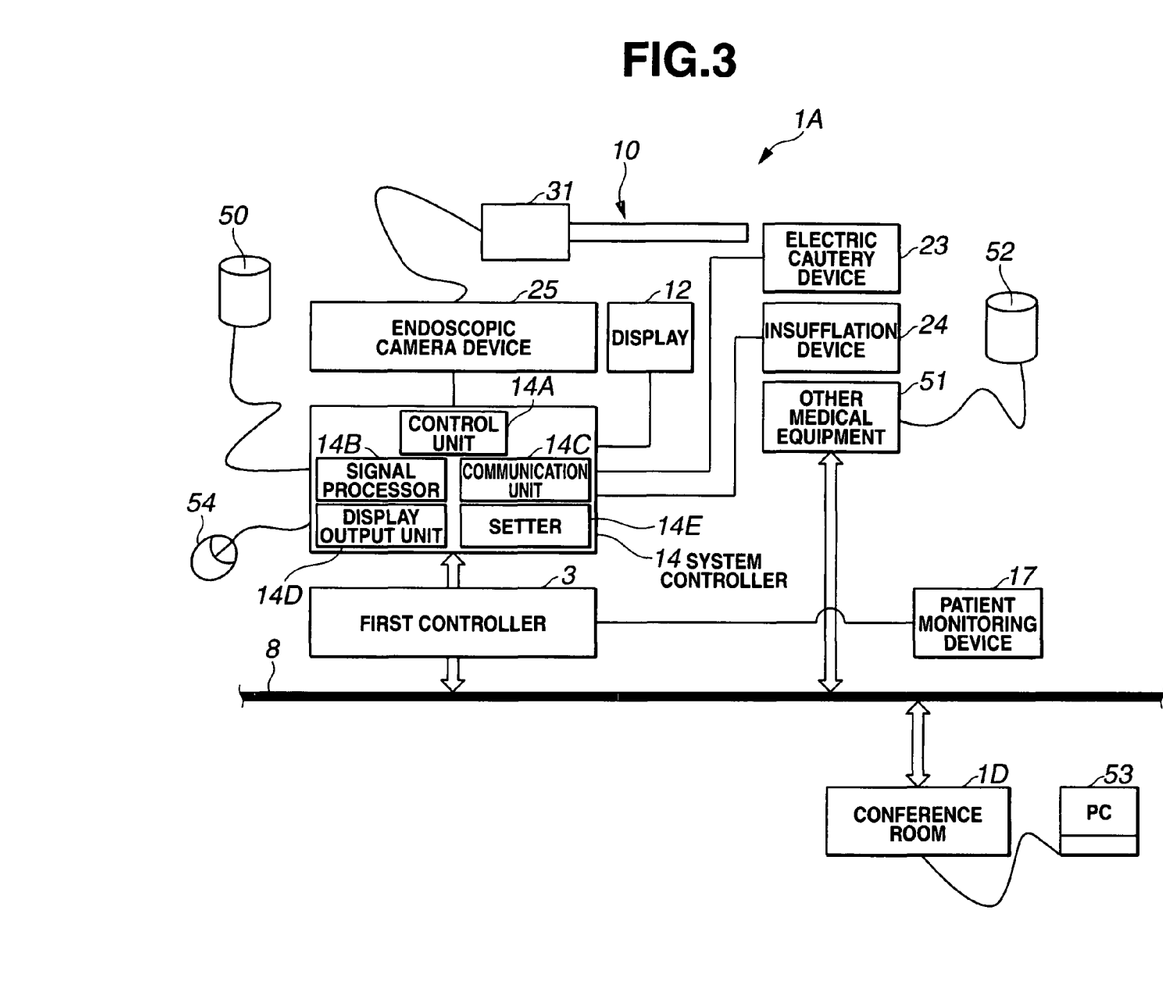
FIG. 3 is a block diagram illustrating a major portion of the medical operation system.
Figure 4:
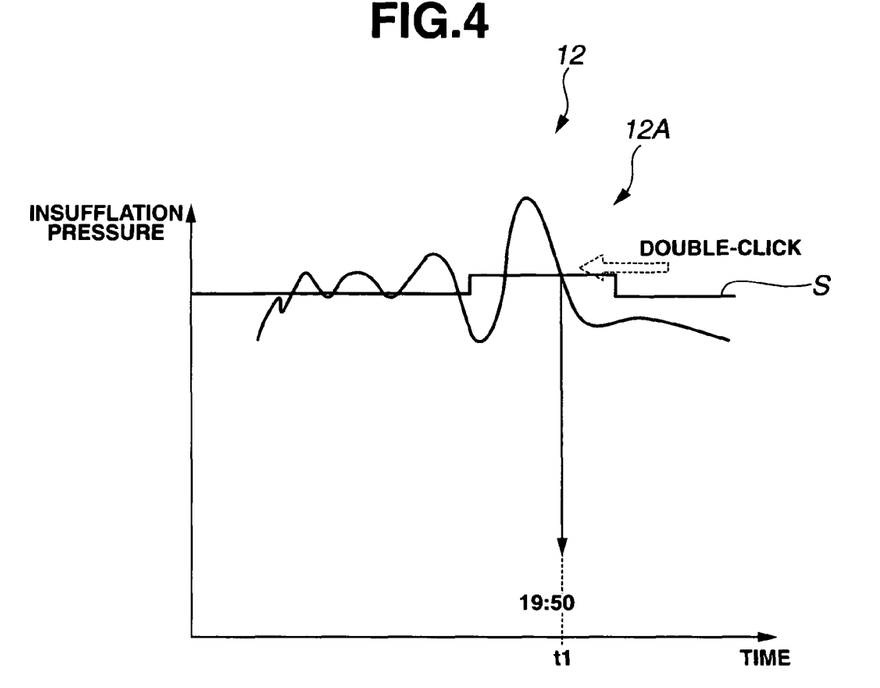
FIG. 4 is a waveform graph of waveforms displayed by a system controller in accordance with the first embodiment of the present invention.
Figure 5:
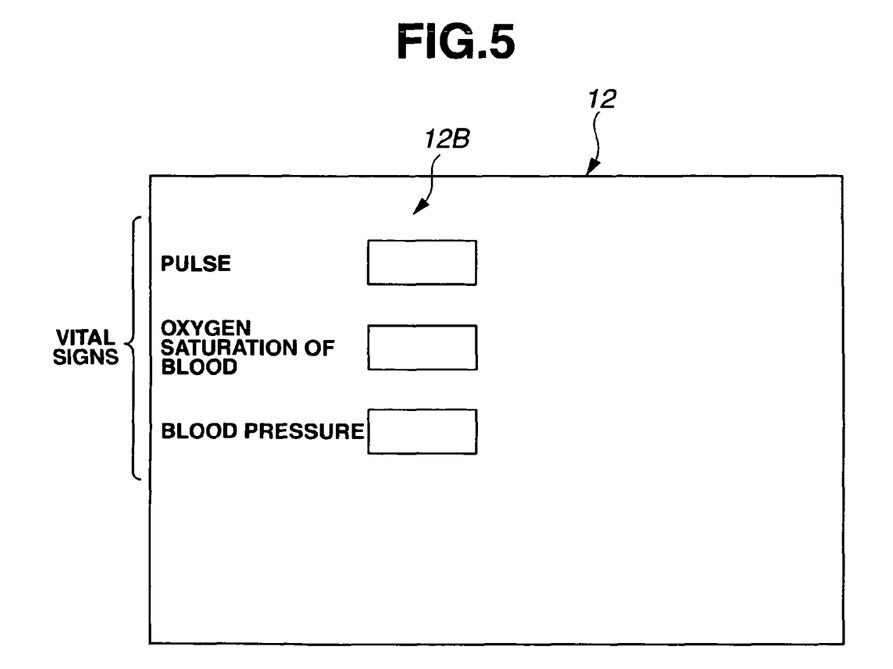
FIG. 5 illustrates on-screen patient information at time specified on the waveform graph of FIG. 4.
Figure 6:
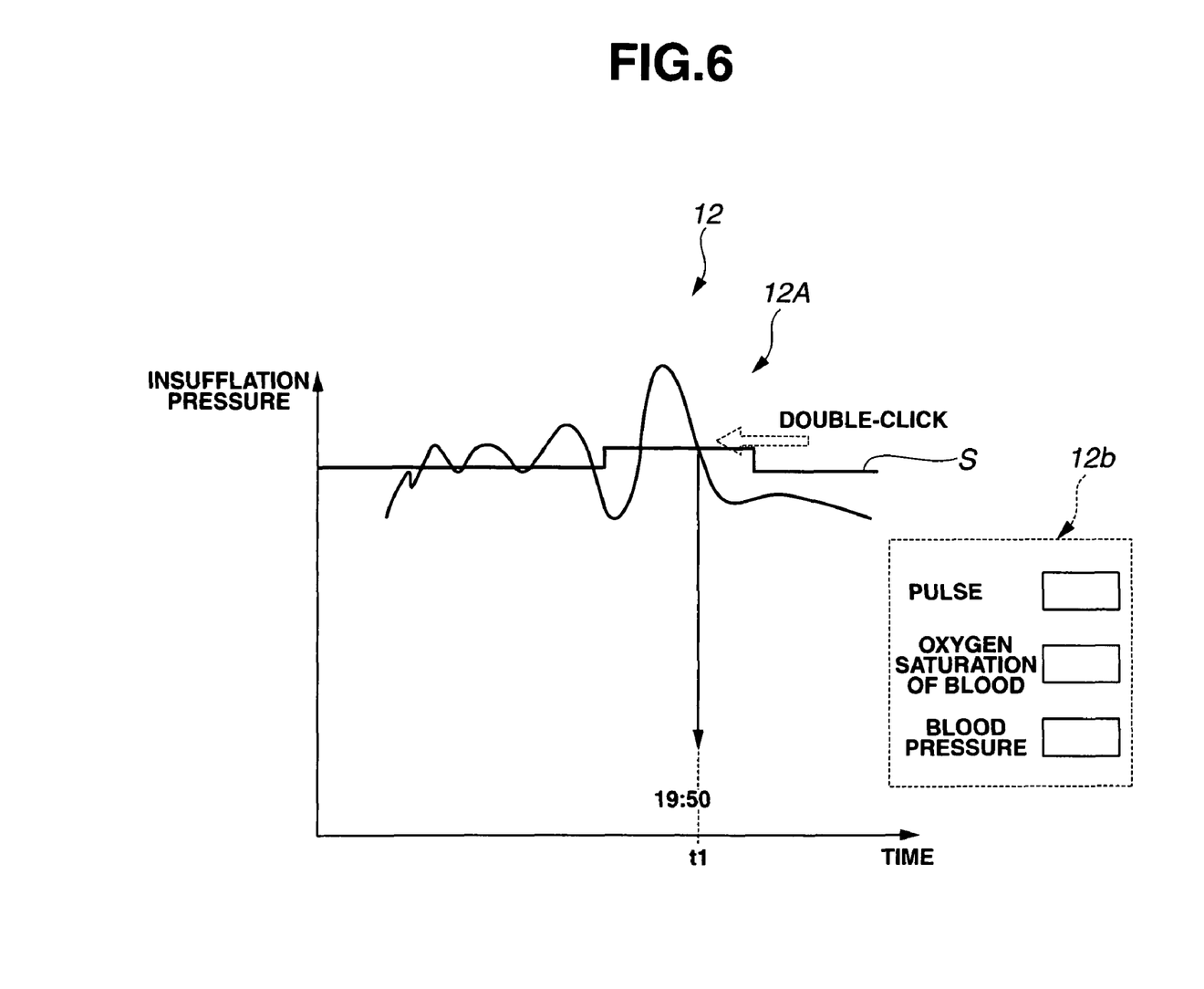
FIG. 6 illustrates the on-screen waveform of FIG. 4 with the patient information of FIG. 5 added thereon.
Figure 7:
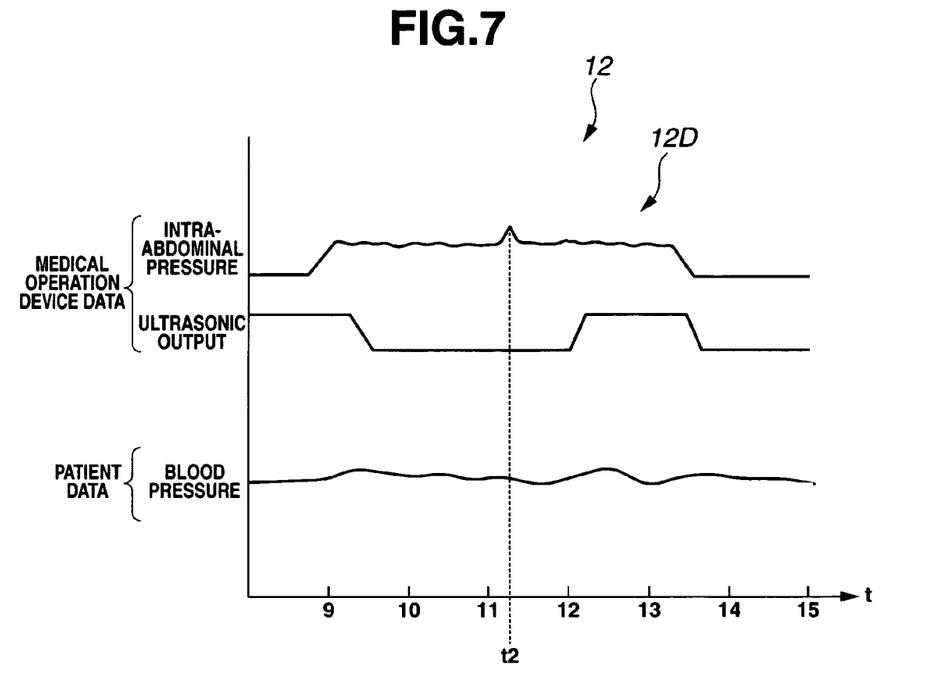
FIG. 7 is a waveform graph with data of a predetermined medical operation device and the patient information shown together.
Figure 8:
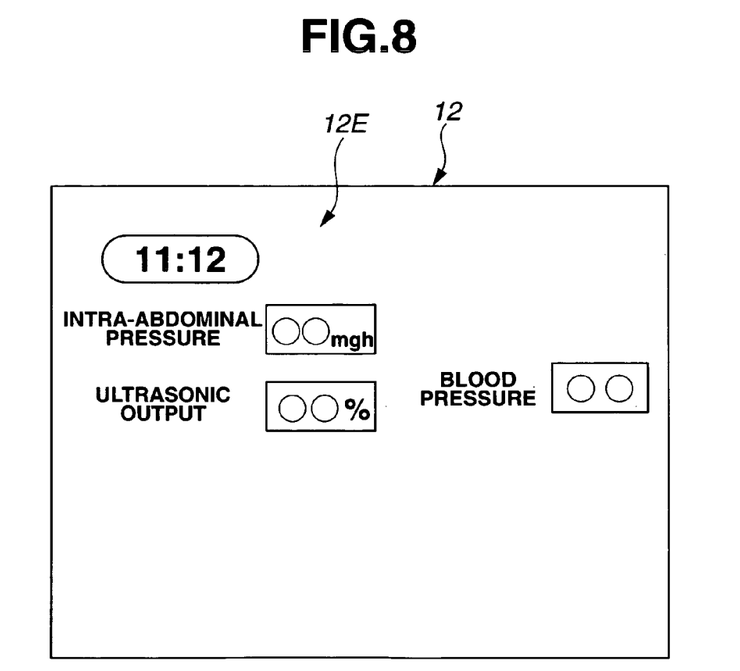
FIG. 8 illustrates on-screen patient information at time specified on the waveform graph of FIG. 7.
Figure 9:
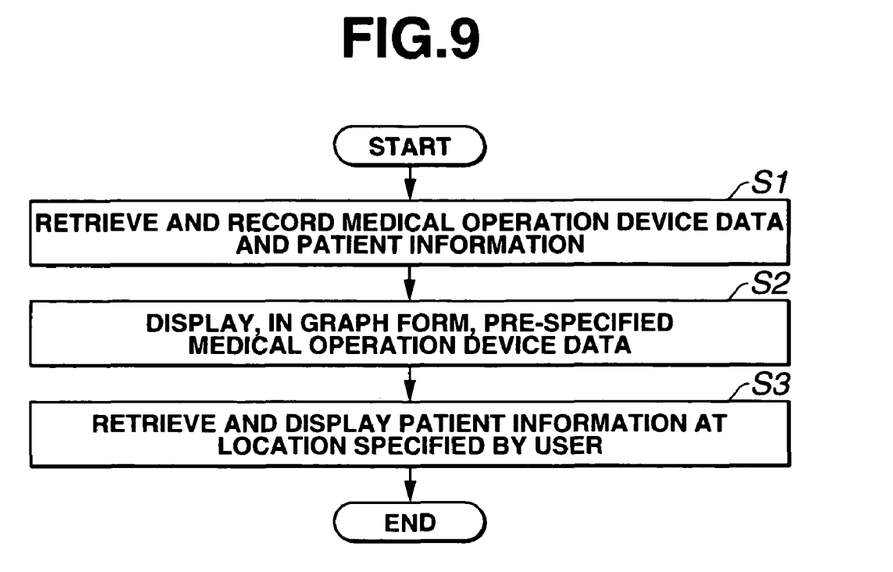
FIG. 9 is a flowchart of a control process of a system controller in accordance with the first embodiment of the present invention.

FIGS. 1-9 illustrate a medical operation system 1 of a first embodiment of the present invention. FIG. 1 is a block diagram illustrating an entire configuration of the medical operation system 1 in accordance with a first embodiment of the present invention. FIG. 2 illustrates a configuration of a specific example of the medical operation system 1 installed in a first operating room of FIG. 1. FIG. 3 is a block diagram illustrating a major portion of the medical operation system 1. FIG. 4 illustrates waveforms displayed by a system controller in accordance with the first embodiment of the present invention. FIG. 5 illustrates on-screen patient information at time specified on the waveform graph of FIG. 4. FIG. 6 illustrates the on-screen waveform of FIG. 4 with the patient information of FIG. 5 added thereon. FIG. 7 is a waveform graph with data of a predetermined medical operation device and the patient information shown together. FIG. 8 illustrates on-screen patient information at time specified on the waveform graph of FIG. 7. FIG. 9 is a flowchart of an example of a control process of the system controller in accordance with the first embodiment of the present invention.

As shown in FIG. 1, the medical operation system 1 of a first embodiment of the present invention includes a first operating room 1A that is used to perform a medical operation under endoscopic observation, second and third operating rooms 1B and 1C within the same hospital as the first operating room 1A, a support room (hereinafter referred to as conference room) 1D installed at a remote and different place from the first through third operating rooms 1A-1C, a first controller 3 installed in the first operating room 1A for retrieving patient information (regarding patient vital signs) generated in the operating rooms 1A-1C, a medical operation server 4 installed at a place different from the first operating room 1A, for accumulating a variety of treatment information obtained by the first controller 3 and generating medical records, a hospital server 5, installed at a place different from the location of the medical operation server 4, for referencing medical record information obtained from the medical operation server 4, a world-wide web (WEB) server 7 for establishing a link to the Internet via an intra-hospital communication line 6, another conference room (not shown) linked to the first controller 3 and a signal transmitter 16 via a communication line 9, an endoscopic system 10 installed in the first operating room 1A, and a system controller 14 contained in the endoscopic system 10 for controlling a plurality of medical operation devices 13 and an endoscope 30.

In the medical operation system 1, the first controller 3 is connected to the second operating room 1B, the third operating room 1C, the conference room 1D, and the medical operation server 4 via an operating room communication line 8. The medical operation server 4 is connected to the hospital server 5 via the intra-hospital communication line 6.

Each of the communication lines 6 and 8 may be any of communication lines including a public telephone line, a dedicated line, and a local area network (LAN). The hospital server 5 may be installed at the same location as the medical operation server 4. As an operation support room, the conference room 1D is located in the same hospital to support the first operating room 1A. Alternatively, the conference room 1D may be arranged at a remote place external to the hospital.

In accordance with the present embodiment, the system controller 14 provides a control function for controlling a plurality of medical equipments, such as surgical devices, in response to a control instruction, a communication function for transmitting and receiving data between each of the plurality of medical equipments and the control function, a function for recording, together with time information, information transmitted from and received to the medical equipment (device information and patient information) on a storage unit as information recording means, a signal processing function for extracting and processing predetermined required information from the information recorded on the storage unit, and generating time-series data such as a graphical display of waveforms varying along time axis, and a display output function for visualizing the time-series data and outputting the visualized time-series data to a display.

The endoscopic system 10 includes the endoscope 30, a video and light-source device 11, a display 12, the medical operation devices 13 as a medical equipment, a video file section (not shown) as information recording means, and the system controller 14.

The system controller 14 in the endoscopic system 10 includes the video and light-source device 11, the display 12 for displaying an image signal obtained by the video and light-source device 11, the medical operation devices 13 including an electric cautery device, an insufflation device, an ultrasonic surgical devices, etc., and the video file section (not shown) as recording means for recording an audio signal and a video signal from the endoscope 30. The video and light-source device 11 is connected to the endoscope 30. The video and light-source device 11 directs illumination light onto the intracavital region of a patient through the distal end of the endoscope 30. The endoscope 30 captures an image of the intracavital region of the patient and the video and light-source device 11 acquires an image signal as an endoscopic image. The system controller 14 retrieves device information such as measurement information provided by the medical operation devices 13.

The system controller 14 controls the video and light-source device 11, the display 12, the medical operation devices 13, and the video file section.

The video and light-source device 11 is connected to the endoscope 30, which captures the image of the intracavital region of the patient. The video and light-source device 11 thus acquires the image signal as the endoscopic image while directing the illumination light to the intracavital region through the distal end of the endoscope 30.

The display 12 displays the video signal obtained by the video and light-source device 11. The medical operation devices 13 include the electric cautery device, the insufflation device, and the ultrasonic surgical device. The video file section stores the video signal from the endoscope 30 together with the audio signal.

The system controller 14 connects to a touchpanel 15 as input means for inputting an operational input as a control instruction to the medical operation device 13.

Medical operation device information from the system controller 14 and patient information from a patient monitoring device 17 to be described later are collected by the first controller 3 via a communication line. The medical operation device information and the patient information are transmitted to the medical operation server 4 located at another place via the operating room communication line 8 when medical operation supporting is performed. In accordance with the first embodiment, the medical operation device information and the patient information are also collected by the system controller 14 via the first controller 3.

The patient monitoring device 17 continuously detects and monitors the patient information (regarding vital signs) of a patient, such as blood pressure, cardiac rate, oxygen saturation of blood. The patient monitoring device 17, connected to the first controller 3, may also be connected to the system controller 14.

The video signal captured by the video and light-source device 11 and the video signal acquired from an indoor camera 19 that captures an image of the operating room are input to the first controller 3 and then transferred to the conference room 1D via the operating room communication line 8.

In the medical operation system 1, the transferred endoscopic image as the video signal and the video signal of the image of the operating room are received at the conference room 1D separate from the first operating room 1A, and displayed on a monitor (not shown) there. Thus, surgeons in the conference room 1D can also recognize the corresponding images.

In the medical operation system 1, a video signal and support information for supporting a surgeon who operates the patient in the first operating room 1A are transferred to the first operating room 1A via the operating room communication line 8. The video signal and the support information are displayed to a display 18 to be described later, and used to give a voice instruction via a headset (not shown) containing a microphone and an earphone on a real-time basis to support the operating surgeon.

The video signal obtained from the video and light-source device 11 and the video signal obtained from the indoor camera 19 capturing the image of the operating room are input to the signal transmitter 16 via the first controller 3 and then transferred via the communication line 9 to a remotely located conference room, for example.

One of the display 12 and the display 18 arranged in the first operating room 1A displays not only the medical operation device information obtained by the first controller 3, the patient information obtained by the medical operation server 4, and the endoscopic image signal for operation support coming from the conference room 1D but also information received by the signal transmitter 16 from outside the hospital via the communication line 9.

The medical operation server 4 is connected to the hospital server 5 and the WEB server 7 via the intra-hospital communication line 6. Since the first operating room 1A is linked to the outside world via the WEB server 7 and the Internet, required information is retrieved from the outside world.

The hospital server 5 stores patient registration information from a patient registration terminal 20 in the hospital, and medical operation images including pre-operation images such as magneto-resonance (MR) images, computer tomography (CT) images, and X-ray images, and medical operation images, such as an endoscopic moving image, obtained at a preceding medical operation. The hospital server 5 receives a video signal of an endoscopic image, obtained by the video and light-source device 11, on a real-time basis, and stores the video signal.

The medical operation server 4 reads registered information regarding the name of a patient to be operated, the data of birth of the patient, and a medical record of the patient, and medical-image information regarding the patient from the hospital server 5 via the intra-hospital communication line 6.

The first controller 3 generally controls the first operating room 1A. More specifically, the first controller 3 performs storage control for controlling the storing of data of the endoscopic image and the patient information, display control for generating and displaying a video signal on the display 18, drive control for controlling the driving of the patient monitoring device 17 and the system controller 14, transfer control for transferring the patient information (regarding vital signs) and the medical operation device information, input and output control for outputting and inputting video information, containing the endoscopic image, and support information from and to the signal transmitter 16, and transmit and receive control for transmitting and receiving information via the operating room communication line 8.

The first controller 3 is connected to an input device 3a. The input device 3a may include at least one of a keyboard, a magnetic card reader, an optical card reader, and an integrated-circuit (IC) card reader. Using the input device 3a, the patient information including a medical record number of a patient (ID number), and the name of the patient and the like is entered.

The input device 3a may be connected to the system controller 14. With the input device 3a connected to the system controller 14, the patient information is transmitted from the system controller 14 to the first controller 3.

The structure of the endoscopic system 10 installed in the first operating room 1A is specifically described with reference to FIG. 2.

A patient bed 10A on which a patient lies down, and the endoscopic system 10 are arranged in the first operating room 1A. The endoscopic system 10 includes a first cart 21 and a second cart 22.

A plurality of endoscope supporting devices for observation, examination, treatment, and recording of the patient are mounted on the carts 21 and 22.

The first cart 21 carries an electric cautery device 23, and an insufflation device 24, forming the medical operation devices 13 to be controlled, and an endoscopic camera device 25, a light-source device 26, a video-tape recorder (VTR) 27, etc., forming the video and light-source device 11, and a gas container 28 filled with carbon dioxide gas ($CO_2$).

The endoscopic camera device 25 is connected to a first endoscope 31 via a camera cable 31a. The light-source device 26 is connected to the first endoscope 31 via a light-guide cable 31b.

The first cart 21 further carries the display 12, a first intensive display panel (hereinafter simply referred to display panel) 29, a touchpanel 15, etc. For example, the display 12 is a television monitor displaying the endoscopic image, the medical operation device information, and the patient information.

The display panel 29 is display means for selectively displaying all of medical operation related data. For example, the touchpanel 15 is composed of a display such as a liquid-crystal display, and a touch sensor integrated into a unitary body with the display. The touchpanel 15 serves as a central operation device that is operated by nurses in an unsterilized area.

The system controller 14 is mounted on the first cart 21. The system controller 14 is connected to the electric cautery device 23, the insufflation device 24, the endoscopic camera device 25, the light-source device 26, and the VTR 27 via a communication line (not shown) for two-way communications.

A control unit 14A, such as a central processing unit (CPU), in the system controller 14 controls each device in accordance with a control program.

A headset type microphone 41 can be connected to the system controller 14. The system controller 14 recognizes a voice input via the microphone 41, and controls each device in response to a voice instruction from an operating surgeon.

The system controller 14 has the function of controlling each device in response to the control instruction.

The second cart 22 carries an endoscopic camera device 33 constituting a controlled device, a light-source device 34, an image processor 35, a display 36, and a second display panel 37.

The endoscopic camera device 33 is connected to a second endoscope 32 via a camera cable 32a. The light-source device 34 is connected to the second endoscope 32 via a light-guide cable 32b.

The display 36 displays an endoscopic image captured by the endoscopic camera device 33. The second display panel 37 selectively displays all data of a medical operation currently under way.

The endoscopic camera device 33, the light-source device 34 and the image processor 35 are connected to a relay unit 38 mounted on the second cart 22 via a communication line (not shown). The relay unit 38 is connected to the system controller 14 mounted on the first cart 21 via a relay cable 39.

The system controller 14 generally controls the endoscopic camera device 33, the light-source device 34 and the image processor 35 mounted on the second cart 22 and the electric cautery device 23, the insufflation device 24, the endoscopic camera device 25, the light-source device 26, and the VTR 27 mounted on the first cart 21. When communications are performed between the system controller 14 and each of these devices, the system controller 14 displays, on the LCD of the touchpanel 15, setting state of connected devices and a setting screen of operation switches. When a touch sensor in a predetermined area is operated in response to the touching of a predetermined switch by an operation, a set value, for example, is modified in the system controller 14.

A remote controller 40 is a second central operation device operated by an operating surgeon in the sterilized area. The operating surgeon can thus control another actively linked device using the system controller 14.

The system controller 14 is cable connected to the patient monitoring device 17 via the first controller 3. As will be described later, the system controller 14 analyzes the patient information (vital signs), such as the cardiac rate, the oxygen saturation of blood, and the blood pressure of the patient obtained from the patient monitoring device 17, and causes one of the display 12 and the display 18 (FIG. 1) to display the analysis results.

An infrared communication port (not shown) is attached to the system controller 14. The infrared communication port is arranged at a location, where an infrared light beam can be easily directed, for example, near the display 12. The infrared communication port is cable connected to the system controller 14.

The system controller 14 is connected to the first controller 3 (FIG. 1) via a cable 14F (FIGS. 1 and 2) for communication.

The endoscopic system 10 of the present embodiment includes the first and second controllers 3 and 14. The present invention is not limited to this arrangement. The first controller 3 may be integrated with the system controller 14. In this case, the system controller 14, connected to the medical operation devices 13 using a plurality of communication lines, generally controls the medical operation devices 13.

A major portion of the medical operation system 1 is described below with reference to FIG. 3.

The system controller 14 in the medical operation system 1 is connected to a storage unit (information recorder) 50 as shown in FIG. 3.

The storage unit 50 stores, together with time data, the medical operation device information such as measurement information of the electric cautery device 23 and the insufflation device 24 (including output set values and intra-abdominal pressure), the patient information (vital signs), such as the blood pressure, the cardiac rate, and the oxygen saturation of blood of the patient monitored by the patient monitoring device 17, and the endoscopic image data.

The writing and reading of the above-described information and the endoscopic image data to and from the storage unit 50 are controlled by the system controller 14. The system controller 14 controls the storage unit 50 so that the medical operation device information, the patient information, and the endoscopic image data are updated, and continuously stored for a predetermined period of time. The time data is retrieved from a timer (not shown) arranged in the system controller 14.

As shown in FIG. 3, if another medical equipment 51 is connected via the operating room communication line 8, the measurement information of the other medical equipment 51 is supplied to the system controller 14 via the operating room communication line 8, and the first controller 3. A storage unit 52 connected to the other medical equipment 51 is substantially identical to the storage unit 50, and stores measurement information. The writing of information to and reading information from the storage unit 52 are also controlled by the system controller 14.

The conference room 1D is equipped with a personal computer 53. When data is analyzed in the conference room 1D, the personal computer 53 communicates with the system controller 14 to perform one of control processes for acquiring, displaying, and recording the required information and endoscopic image data.

The system controller 14 of the present embodiment includes a timer (not shown) for measuring time, a control unit 14A, a signal processor 14B, a communication unit 14C, a display output unit 14D, and a setter 14E. The control unit 14A controls a plurality of medical equipments in response to an operation command, and causes the storage unit 50 as an information recorder to store, together with time information, the information of the medical equipments transmitted by and received by the medical equipments. The communication unit 14C exchanges data in two-way communications between each of the plurality of medical equipments and the control unit 14A. The signal processor 14B extracts predetermined information from the information stored on the storage unit 50, and processes the predetermined information to generate time-series data. The display output unit 14D visualizes the time-series data from the signal processor 14B and outputs the visualized time-series data to the display 12. The setter 14E sets a threshold value to information regarding a predetermined medical equipment.

The signal processor 14B performs a process on the medical operation device information as the supplied time-series data to display the medical operation device information in a waveform graph, and a process to compare graphically the medical operation device information with the patient information in time axis.

The system controller 14 causes one of the display 12 and the display 18 to display the process results of the time-series data provided by the signal processor 14B.

The time-series data is not limited to waveform data. The time-series data may be in any form representing a change. For example, the time-series data may be a list of data values with time, bars representing the magnitude of data with time, etc.

FIG. 4 illustrates an example of a waveform of medical operation device information displayed on a display screen of the display. The medical operation device information in this case is the measurement information of the insufflation device 24 recorded together with time data on the storage unit 50.

The system controller 14 causes one of the display 12 and the display 18 to display a waveform screen 12A based on the detection results of the signal processor 14B. The ordinate of the waveform graph displayed on the waveform screen 12A represents measurement values of the insufflation device 24 while the abscissa represents the time based on the time data.

The system controller 14 causes a set value (threshold value) S of the insufflation device 24, set by the system controller 14 in response to the operation input beforehand by the surgeon, to be displayed on the waveform screen 12A.

In accordance with the present embodiment, the medical operation device information displayed on the waveform screen 12A may the medical operation device information of any medical operation device set beforehand in a medical operation. Any medical operation device from which the medical operation device information is obtained to display a waveform graph is selected.

When a mouse 54 (FIG. 3) as a pointing device is operated to double-click on a desired location on the waveform screen 12A of FIG. 4, the system controller 14 switches to a patient information screen 12B displaying the patient information, or to an on-screen display of FIG. 6. The patient information screen 12B displays, together with the time information, the patient information including the blood pressure, the cardiac rate, and the oxygen saturation of blood of the patient stored on the storage unit 50 in a text format.

Since the medical operation system 1 includes the plurality of medical operation devices, time synchronization needs to be established among all devices to perform more detailed examination.

Timers (not shown) of all devices are made synchronized with the time in the system controller 14 at the moment the medical operation system 1 is switched on. More specifically, by communicating with the plurality of medical operation devices, the system controller 14 causes the timers of all medical operation devices to be synchronized with the timer thereof.

In accordance with the present embodiment, the time synchronization method in the medical operation system 1 is not limited to the above-referenced method. Another method may be used to establish time synchronization among the devices.

The operation of the medical operation system 1 of the present embodiment is described below with reference to FIGS. 4 through 9.

A surgeon now switches on the medical operation system 1 of FIG. 1. The system controller 14 in the endoscopic system 10 performs a process step in step S1 by initiating a program of FIG. 9.

In step S1, the system controller 14 communicates with all connected medical operation devices 13 after the medical operation system 1 is powered on, and causes the timers (not shown) of all medical operation devices 13 to be synchronized with the timer (not shown) of the system controller 14.

The system controller 14 causes the storage unit 50 to store, together with the time information, the medical operation device information from each operating medical operation device and the patient information from the patient monitoring device 17.

For example, the storage unit 50 stores the medical operation device information, such as the measurement information from the electric cautery device 23 and the insufflation device 24, and the patient information, such as vital signs, regarding the blood pressure, the cardiac rate, and the oxygen saturation of blood level of the patient obtained by the patient monitoring device 17.

If a command to verify and analyze the content of a medical operation of a patient is entered to the touchpanel 15 or the like by a surgeon, the system controller 14 performs a process step in step S2.

In step S2, the system controller 14 reads, from the storage unit 50, the medical operation device information of a medical operation device specified beforehand, and the patient information so that the signal processor 14B displays the read information in a waveform graph.

As shown in FIG. 4, the system controller 14 causes one of the display 12 and the display 18 to display the waveform screen 12A based on the detection results of the signal processor 14B. In this case, a set value S of the insufflation device 24 set by the system controller 14 in response to an operation of the surgeon is shown on the waveform graph on the waveform screen 12A as shown in FIG. 4.

By viewing the waveform screen 12A, the surgeon can easily compare the actual measurement value from the patient by the insufflation device 24 with the set value S.

When the mouse 54 (FIG. 3) double-clicks on a desired location on the waveform screen 12A of FIG. 4, the system controller 14 switches from the waveform screen 12A to the patient information screen 12B (FIG. 5) or the on-screen display where a patient information screen 12b is superimposed as shown in FIG. 6 (step S3).

More specifically, when the surgeon double-clicks on the location of time t1 on the waveform graph, the system controller 14 switches to the patient information screen 12B (FIG. 5) corresponding to time t1 or the on-screen display where the patient information screen 12b (FIG. 6) is superimposed.

By displaying the patient information corresponding to the desired location, the actual state of the patient is recognized.

In accordance with the present embodiment, the patient information is based on a single medical operation device. Alternatively, the patient information of a plurality of medical operation devices may be superimposed in the waveform graph in time axis as shown in a waveform screen 12D of FIG. 7. As shown in the waveform screen 12D, the intra-abdominal pressure, the medical operation device information of ultrasonic output, and the blood pressure as the patient information are displayed in the waveform graph.

When time t2 in the waveform graph is double-clicked, the system controller 14 switches to an information screen 12E displaying the patient information and the medical operation device information at time t2 or an on-screen display.

In accordance with the present embodiment, the system controller 14 switches from the waveform graph to the patient information screen (FIG. 5) or the on-screen display (FIG. 6). The present invention is not limited to this method. The system controller 14 displays measurement values and set values of the medical operation devices at any point of time and detailed medical operation device information rather than the patient information. The display mode is easily switchable.

In accordance with the present embodiment, the medical operation device information is compared with the patient information in time axis. The surgeons can thus verify and analyze the content of the medical operation more in detail based on a variety of pieces of data of the medical operation devices.

As shown in FIG. 4, the medical operation system 1 of the first embodiment of the present invention displays the set value (threshold value) S set in the waveform screen 12A while the operation command from the surgeon is manually input on the waveform graph.

In the medical operation system 1 of a second embodiment of the present invention, the patient information at a region requiring analysis can be automatically displayed by comparing beforehand the set value (threshold value) S of a medical operation device to be used in a medical operation, with the medical operation device information of the medical operation device currently in use. By searching for and specifying regions requiring analysis, the patient information at the specified region is displayed. The second embodiment of the present invention is described below referring to FIG. 10.

Second Embodiment

Figure 10:
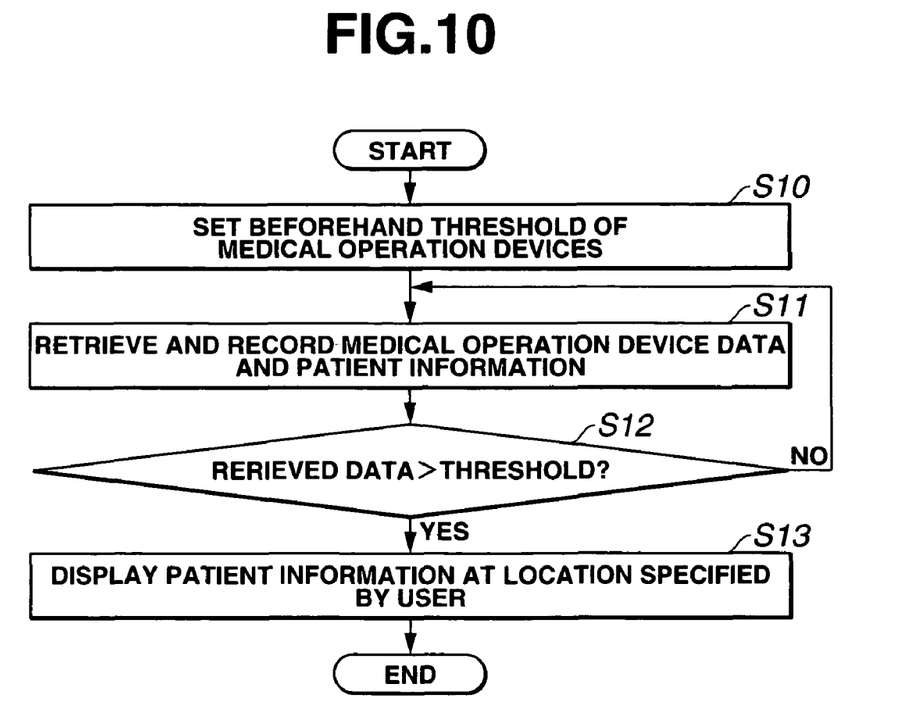
FIG. 10 is a flowchart illustrating an example of a control process of a system controller in a medical operation system in accordance with a second embodiment of the present invention.

An example of a control process of the system controller 14 in a medical operation system 1 of the second embodiment of the present invention is described below with reference to a flowchart of FIG. 10.

The medical operation system 1 of the second embodiment is substantially identical to the medical operation system 1 of the first embodiment except a control process of the system controller 14.

The operation of the medical operation system 1 in accordance with the second embodiment is described below with reference to FIG. 10.

The medical operation system 1 of FIG. 1 is now powered on by a surgeon or the like. The system controller 14 in the endoscopic system 10 initiates a program of FIG. 10 to perform a process step in step S10.

In step S10, the system controller 14 communicates with all connected medical operation devices after the medical operation system 1 is powered on, and causes the timers (not shown) of all medical operation devices to be synchronized with the timer (not shown) of the system controller 14.

The system controller 14 sets a threshold value for a medical operation device to be used by the surgeon, and proceeds to step S11.

In step S11, the system controller 14 causes the storage unit 50 to store, together with the time information, the medical operation device information from each operating medical operation device and the patient information from the patient monitoring device 17.

For example, the storage unit 50 stores the medical operation device information, such as the measurement information from the electric cautery device 23 and the insufflation device 24, and the patient information regarding the blood pressure, the cardiac rate, and the oxygen saturation of blood level of the patient obtained by the patient monitoring device 17. The storage unit 50 thus stores the medical operation device information and the patient information.

If a command to verify and analyze the content of a medical operation of a patient is entered to the touchpanel 15 or the like by a surgeon, the system controller 14 performs a process step in step S12.

In step S12, the system controller 14 reads, from the storage unit 50, the medical operation device information of a medical operation device specified beforehand, and the patient information so that the signal processor 14B graphically displays the read information in the waveform graph.

As shown in FIG. 4, the system controller 14 causes one of the display 12 and the display 18 to display the waveform screen 12A based on the detection results of the signal processor 14B. In this case, a set value (threshold) S of the insufflation device 24 set by the system controller 14 in response to an input operation of the surgeon is shown on the waveform graph on the waveform screen 12A. By viewing the waveform screen 12A, the surgeon can easily compare the actual measurement value from the patient by the insufflation device 24 with the set value S.

The system controller 14 compares the measurement value of the insufflation device 24 displayed on the waveform screen 12A with the set value S. If the measurement value is lower then the set value S, processing returns to step S11. If the measurement value is higher than the set value S, a location corresponding to the time on the waveform graph is recognized, and processing proceeds to step S13. More specifically, if the measurement value is higher than the set value S, a change occurs in the data of the medical operation device and analysis needs to be performed.

In step S13, the system controller 14 automatically specifies the location recognized in step S12 on the waveform screen 12A of FIG. 4, and switches from the waveform screen 12A to the patient information screen 12B (FIG. 5) or the on-screen display where the patient information screen 12b is superimposed as shown in FIG. 6.

Alternatively, the system controller 14 may indicate regions in need of analysis recognized in step S12 using a plurality of markers, and prompts the surgeon to select any of the marked regions. Then, as described above, the system controller 14 displays, instead of the waveform screen 12A, the patient information screen 12B (FIG. 5) responsive to the location specified by the surgeon on the waveform screen 12A of FIG. 4, or the on-screen display where the patient information screen 12b is superimposed as shown in FIG. 6.

The second embodiment provides the same advantages as those of the first embodiment. Furthermore, in accordance with the second embodiment, the location on the displayed waveform graph requiring analysis is automatically recognized. The patient information at that location is automatically displayed or the patient information at a manually selected location is displayed. Time required to verify and analyze the content of a medical operation is shortened.

In the second embodiment, the medical operation system 1 flexibly selects between an automatic mode and a manual mode for displaying the patient information. One of the automatic mode and the manual mode is set beforehand as necessary.

One of the display 12 and the display 18 displays the waveform graph in accordance with the first and second embodiments. Not only the waveform graph but also the endoscopic image recorded with time may be displayed at the same time. With this arrangement, the content of the medical operation is verified and analyzed in more detail.

Having described the preferred embodiments of the invention referring to the accompanying drawings, it should be understood that the present invention is not limited to those precise embodiments and various changes and modification thereof could be made by one skilled in the art without departing from the spirit or scope of the invention as defined in the appended claims.

What is claimed is:

1. A medical operation system comprising:
a controller for controlling a plurality of surgical equipments;
a communication unit for transmitting and receiving data between each of the plurality of surgical equipments and the controller in two-way communications;
an information recorder which records, together with time information, patient information representing a state of patient and surgical equipment information to be used for a preset surgery in the plurality of surgical equipments transmitted and received by the communication unit;
a signal processor which extracts predetermined information from the information recorded on the information recorder and processes the predetermined information to generate time-series data which changes on time axis;
a display output unit for visualizing surgical equipment information in the time-series data output from the signal processor and outputting the visualized time-series data to a display; and
an instruction portion capable of specifying operations on a display screen of the display outputted by the display output unit,
wherein the controller includes: an extraction unit for extracting the patient information corresponding to the arbitrary location of the surgical equipment information on the display screen, the arbitrary location being specified by the instruction portion; and a display switching unit for switching to display the patient information extracted by the extraction unit on the display screen instead of the surgical equipment information when specified by the instruction portion.

2. The medical operation system according to claim 1, wherein the controller displays switching between the patient information screen for displaying the patient information and surgical equipment information screen for displaying the surgical equipment information.

3. The medical operation system according to claim 1, wherein the time-series data comprises waveform data.

4. A medical operation system comprising:
a controller for controlling a plurality of surgical equipments;
a communication unit for transmitting and receiving data between each of the plurality of surgical equipments and the controller in two-way communications;
an information recorder which records, together with time information, patient information representing a state of patient and surgical equipment information to be used for a preset surgery in the plurality of surgical equipments transmitted and received by the communication unit;
a signal processor which extracts predetermined information from the information recorded on the information recorder and processes the predetermined information to generate time-series data which changes on time axis;
a display output unit for visualizing surgical equipment information in the time-series data output from the signal processor and outputting the visualized time-series data to a display; and
an instruction portion capable of specifying operations on a display screen of the display outputted by the display output unit,
wherein the controller includes: an extraction unit for extracting the patient information corresponding to the arbitrary location of the surgical equipment information on the display screen, the arbitrary location being specified by the instruction portion; and
a superimposing unit for providing an on-screen display of a patient information screen for displaying the patient information on a surgical equipment information screen for displaying the surgical equipment information.

5. A medical operation system comprising:
a controller for controlling a plurality of surgical equipments;
a communication unit for transmitting and receiving data between each of the plurality of surgical equipments and the controller in two-way communications;
an information recorder which records, together with time information, patient information representing a state of patient and surgical equipment information to be used for a preset surgery in the plurality of surgical equipments, transmitted and received by the communication unit;
a signal processor which extracts predetermined information from the information recorded on the information recorder and processes the predetermined information to generate time-series data which changes on a time axis;
a display output unit for visualizing surgical equipment information in the time-series data output from the signal processor and outputting the visualized time-series data to a display; and
a setting unit capable of setting a threshold value to a predetermined surgical equipment information,
wherein the controller includes: a comparison unit for comparing a threshold value set by the setting unit with a value of the extracted surgical equipment information; an extraction unit for automatically extracting the patient information of a display location recognized based on the result of comparison; and a display switching unit for switching to display the patient information extracted by the extraction unit on the display screen instead of the surgical equipment information.

6. The medical operation system according to claim 5, wherein the time-series data comprises waveform data.

7. A medical operation system comprising;
control means for controlling a plurality of surgical equipments in response to a control instruction;
communication means for transmitting and receiving data between each of the plurality of surgical equipments and the control means;
information recording means for recording, together with time information, patient information representing a state of a patient and surgical equipment information to be used for a preset surgery in the plurality of surgical equipments, transmitted from and received by the communication means;
signal processing means for extracting required predetermined information from the information recorded on the information recording means and processing the predetermined information to generate time-series data which changes on a time axis;
display output means for visualizing surgical equipment information in the time-series data and outputting the visualized time-series data to a display; and
instruction means capable of specifying operations on a display screen of the display outputted by the display output means,
wherein the control means includes: extraction means for extracting the patient information corresponding to the arbitrary location of the surgical equipment information on the display screen, the arbitrary location being specified by the instruction means; and display switching means for switching to display the patient information extracted by the extraction means on the display screen instead of the surgical equipment information when specified by the instruction means.

8. The medical operation system according to claim 7, wherein the control means displays switching between the patient information screen for displaying the patient information and surgical equipment information screen for displaying the waveform data.

9. The medical operation system according to claim 7, wherein the time-series data comprises waveform data.

10. A medical operation system comprising;
control means for controlling a plurality of surgical equipments in response to a control instruction;
communication means for transmitting and receiving data between each of the plurality of surgical equipments and the control means;
information recording means for recording, together with time information, patient information representing a state of a patient and surgical equipment information to be used for a preset surgery in the plurality of surgical equipments, transmitted from and received by the communication means;
signal processing means for extracting required predetermined information from the information recorded on the information recording means and processing the predetermined information to generate time-series data which changes on a time axis;
display output means for visualizing surgical equipment information in the time-series data and outputting the visualized time-series data to a display; and
instruction means capable of specifying operations on a display screen of the display outputted by the display output means, wherein the control means includes: extraction means for extracting the patient information corresponding to the arbitrary location of the surgical equipment information on the display screen, the arbitrary location being specified by the instruction means; and superimposing means for providing an on-screen display of a patient information screen for displaying the patient information on a surgical equipment information screen.

11. A medical operation system comprising:

control means for controlling a plurality of surgical equipments;

communication means for transmitting and receiving data between each of the plurality of surgical equipments and the control means in two-way communications;

information recording means which records, together with time information, patient information representing a sate of patient and surgical equipment information to be used for a preset surgery in the plurality of surgical equipments transmitted and received by the communication means;

signal processing means which extracts predetermined information from the information recorded on the information recording means and processes the predetermined information to generate time-series data which changes on a time axis;

display output means for visualizing surgical equipment information in the time-series data output from the signal processing means and outputting the visualized time-series data to a display; and setting means capable of setting a threshold value to a predetermined surgical equipment information;

wherein the control means includes: comparison means for comparing a threshold value set by the setting means with a value of the extracted surgical equipment information; extraction means for automatically extracting the patient information of a display location recognized based on a result of comparison; and display switching means for switching to display the patient information extracted by the extraction means on the display screen instead of the surgical equipment information.

12. The medical operation system according to claim 11, wherein the time-series data comprises waveform data.

* * * * *